United States Patent [19]

Joslin

[11] 4,332,249

[45] Jun. 1, 1982

[54] FILTER AND VALVE ASSEMBLY FOR HYPODERMIC SYRINGE

[75] Inventor: Joel A. Joslin, Sunset Hills, Mo.

[73] Assignee: Sherwood Medical Industries, Inc., St. Louis, Mo.

[21] Appl. No.: 174,548

[22] Filed: Aug. 1, 1980

[51] Int. Cl.³ .............................................. A61M 5/00
[52] U.S. Cl. ........................... 128/218 NV; 128/272.3
[58] Field of Search ................... 128/215, 221, 218 R, 128/218 N, 218 NV, 234, 272.3; 210/448, 323 R, 323 T; 141/2

[56] References Cited

U.S. PATENT DOCUMENTS

| | | | |
|---|---|---|---|
| 3,736,932 | 6/1973 | Satchell | 128/218 D |
| 4,066,079 | 1/1978 | Chiarolla | 128/221 |
| 4,133,314 | 1/1979 | Bloom et al. | 128/272.3 |
| 4,230,112 | 10/1980 | Smith | 128/272.3 |

Primary Examiner—John D. Yasko
Attorney, Agent, or Firm—Paul L. Gardner

[57] ABSTRACT

Medicinal fluid to be injected into a patient is drawn into a hypodermic syringe barrel through the valve portion of a combination valve and filter assembly, and is ejected through the filter, thereby preventing particulate contamination of the injected medicine. The valve and filter assembly comprises a generally cylindrical, porous filter element, and an elastomeric valve having a generally annular skirt portion overlying the distal end of the filter element and a central portion extending into the central passage in the filter. The central portion of the valve has a slit therein which opens to permit the flow of medicinal fluid therethrough in a distal-to-proximal direction, but closes to block the flow of fluid therethrough in a proximal-to-distal direction.

10 Claims, 8 Drawing Figures

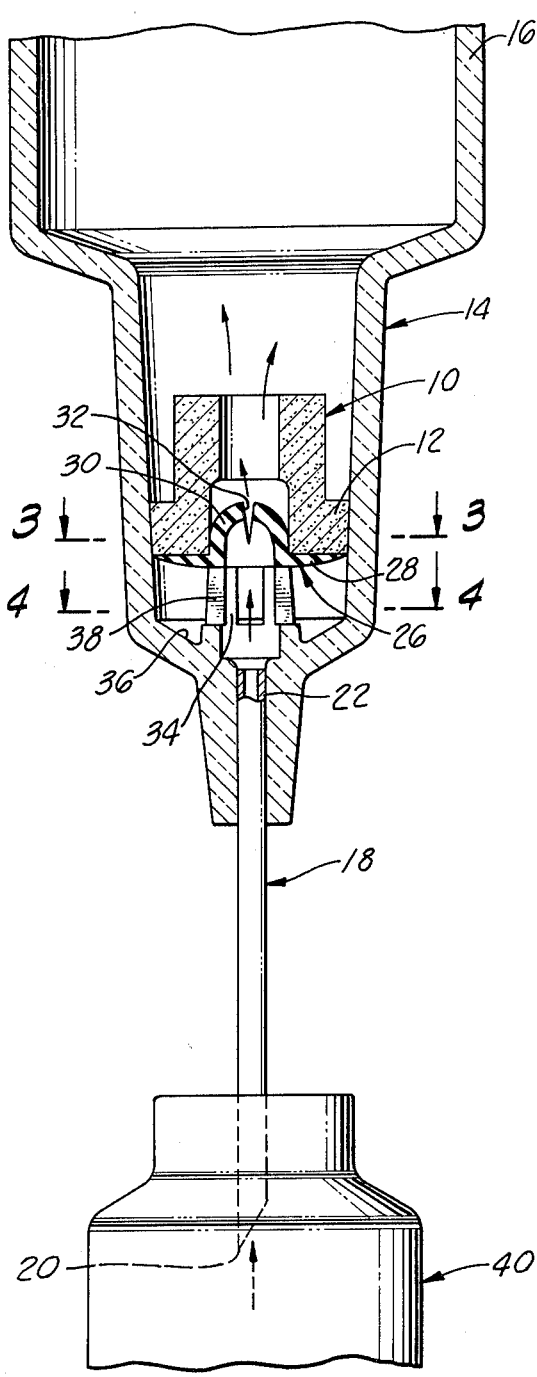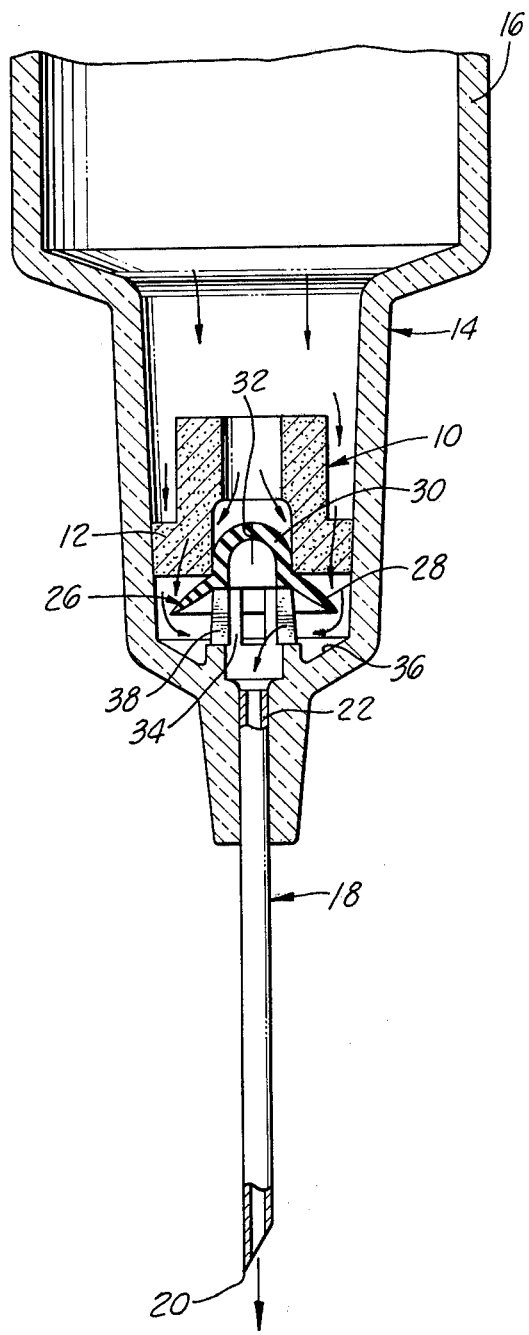
FIG. 1.
FIG. 2.

FILTER AND VALVE ASSEMBLY FOR HYPODERMIC SYRINGE

FIELD OF THE INVENTION

The present invention relates generally to hypodermic syringes and, more specifically, to an improved technique and a combination filter and valve assembly for filling a hypodermic syringe barrel with unfiltered medicinal fluid and filtering the fluid as it is ejected from the syringe barrel.

BACKGROUND OF THE INVENTION

There is a need in the medical field for an inexpensive technique and assembly for injecting uncontaminated medicinal fluid into a patient.

This need exists notwithstanding numerous syringe and filter designs which have been proposed and/or adopted, such as the devices shown in U.S. Pat. Nos. 3,736,932 and 3,817,389.

U.S. Pat. No. 3,817,389 is directed to an improved filter for filtering contamination from medicinal fluid to be injected into a patient. The filter is incorporated in a needle-retaining hub for a hypodermic syringe, whereby the medicinal fluid is filtered to remove contaminants when it is passed through the filter, either when the fluid is drawn from an ampule into the syringe barrel, and/or when the fluid is ejected from the syringe barrel and injected into the patient.

Typically, a two-needle technique is employed in filling the syringe barrel and injecting the patient, whether the filter of the U.S. Pat. No. 3,817,389 type is employed or not. The medicinal fluid is first drawn into the syringe barrel using a first needle, and a second needle is employed for injecting the patient so as to avoid contaminating the medicinal fluid with any foreign matter which may have entered the first needle during filling of the syringe.

U.S. Pat. No. 3,736,932 proposes what might be referred to as a single-needle technique utilizing a needle cannula pointed at both ends and an annular filter having its central opening covered by a diaphragm which is adapted to be pierced by the pointed proximal end of the needle cannula. The needle cannula serves as a filter bypass, whereby the filter will not be loaded with contaminant when the medicinal fluid is drawn into the syringe barrel through the needle (or ejected, depending upon whether the filter is bypassed during aspiration or ejection).

A shortcoming of the invention of the U.S. Pat. No. 3,736,932 patent is the necessity for manually manipulating the double-pointed needle cannula and hub assembly between the step of filling of the syringe and the step of injecting the medicinal fluid into the patient.

OBJECTS OF THE INVENTION

In view of the foregoing it is an object of the present invention to provide an efficient, effective, automatic and inexpensive technique and apparatus for injecting a patient with uncontaminated medicinal fluid.

Another object of the present invention is the provision of a combination filter and valve assembly for a hypodermic syringe which retains the advantages of the prior art devices while eliminating the disadvantages thereof.

Other objects and advantages of the present invention will become apparent from review of the following description of a detailed embodiment thereof.

SUMMARY OF THE INVENTION

The foregoing and other objects of the present invention have been realized by the provision of a combination filter and valve assembly which permits aspiration of medicinal fluid into a hypodermic syringe barrel through the valve portion of the assembly, bypassing the filter portion, and subsequent ejection of the medicine through only the filter portion of the device.

BRIEF DESCRIPTION OF THE DRAWINGS

In the drawings:

FIG. 1 is a longitudinal sectional view of one embodiment of the present invention, shown during the step of drawing medicinal fluid through the valve portion of the combination valve and filter assembly of the present invention.

FIG. 2 is a longitudinal sectional view similar to FIG. 1 but illustrating the device during the step of ejecting the medicinal fluid through the filter portion of the assembly.

DESCRIPTION OF PREFERRED EMBODIMENTS

Figure 3:
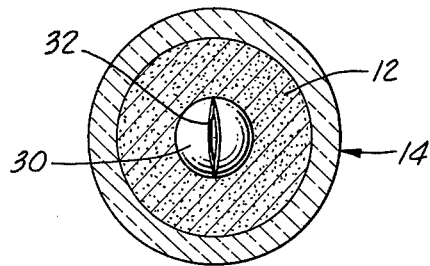
FIG. 3 is a cross-sectional view taken along plane 3—3 of FIG. 1.
Figure 4:
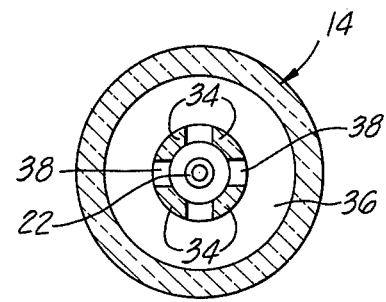
FIG. 4 is a cross-sectional view taken along plane 4—4 of FIG. 1.
Figure 5:
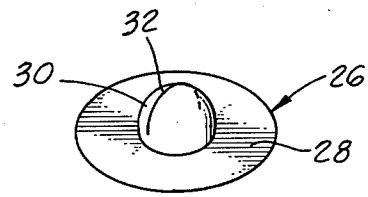
FIG. 5 is an isometric view of the valve portion of the assembly shown in FIG. 1-4.

The embodiment of the present invention depicted in FIGS. 1-5 comprises a generally tubular, porous filter element 10 having an enlarged distal end portion 12 forcefit within the distal end of a needle-carrying hub 14. The needle hub 14 has a proximal end 16 which is adapted to fit on the distal end of a hypodermic syringe (not shown) in a manner which is conventional, per se.

The distal end of the hub 14 has the proximal end 22 of a needle cannula 18 secured therein. The distal end 20 of the needle cannula 18 is pointed; the proximal end 22 is not.

The embodiment illustrated in FIGS. 1-5 further includes a valve member 26 comprising a generally annular skirt portion 28 which normally overlies the distal end surface of the enlarged distal end portion 12 of the filter 10, and a generally hemispherical, proximally-projecting central portion 30 having a central slit 32 therein.

The inner circumferential portion of the annular skirt 28 of the valve member 26 is supported by a plurality of circumferentially-spaced proximally-extending support posts 34, 34, 34, 34 (FIG. 4) formed on the distal end wall 36 of the hub 14.

In operation, the embodiment shown in FIGS. 1-5 functions in the following manner. When it is desired to fill a hypodermic syringe with medicine to be injected into a patient, the proximal end 16 of the hub 14 is seated on the distal end of a conventional hypodermic syringe (not shown) and the pointed end 20 of the needle cannula 18 is inserted through the conventional self-sealing diaphragm in an ampule 40 containing the medicine. Thereafter, the plunger of the syringe (not shown) is drawn in a proximal direction in the syringe barrel to create sub-atmospheric pressure within the hub 14 and syringe barrel (not shown) whereby the medicinal fluid will be suctioned through the needle cannula 18, through the slit 32 in the center of the hemispherical central portion 30 of the elastomeric valve 26, through the hub 14, and into the syringe barrel (not shown), as shown by the flow arrows in FIG. 1.

The needle cannula 18 is thereafter withdrawn from the ampule 40 and inserted into the patient to be injected.

When the plunger (not shown) is moved in a distal direction within the syringe barrel (not shown) to inject the patient, the medicinal fluid will be ejected from the syringe barrel through only the filter 10, as illustrated by the flow arrows in FIG. 2. The fluid pressure against the slitted central hemispherical portion 30 of the valve will maintain the slit 32 closed. It will be noted from FIG. 2 that the flow of medicinal fluid under pressure through the distal end 12 of the filter 10 will displace the peripheral skirt 28 to permit flow of the medicine through the spaces 38 between support posts 34 (FIG. 4), through the needle cannula 18, and into the patient.

Figure 8:
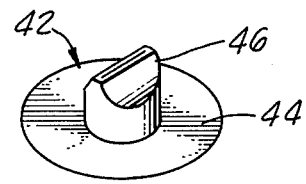
FIG. 8 is an isometric view of the valve portion of the embodiment shown in FIGS. 6 and 7.
Figure 6:
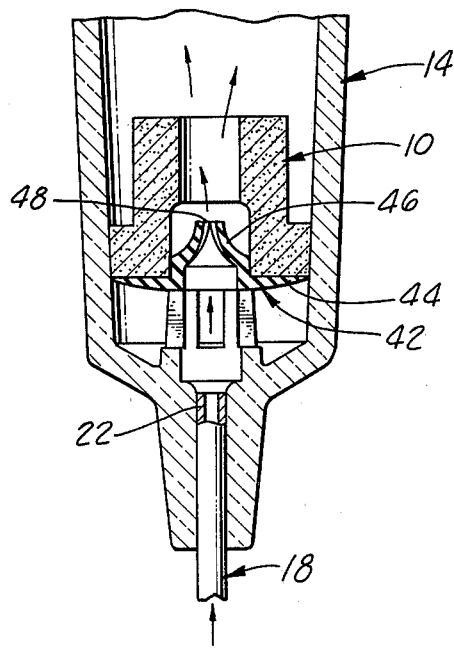
FIG. 6 is a longitudinal sectional view of a second embodiment of the present invention as it appears while medicinal fluid to be ejected is being drawn through the valve portion of the device.
Figure 7:
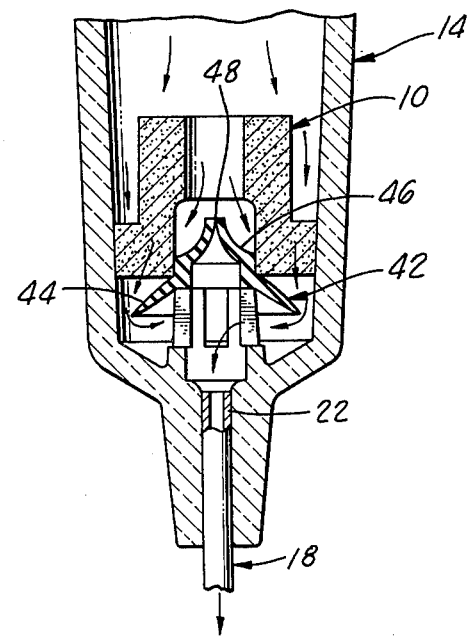
FIG. 7 is a longitudinal sectional view of the second embodiment, similar to FIG. 6, but illustrating the assembly during the step of ejecting medicine through the filter portion of the assembly.

The embodiment illustrated in FIGS. 6–8 differs from the embodiment of FIGS. 1–5 only in the configuration of the central portion of the elastomeric valve 42, which, as best shown in FIG. 8, comprises a generally annular skirt portion 44 and a duckbill-configured central portion 46.

The valve 42 functions in the same manner as the valve 26 of the embodiment of FIGS. 1–5. The syringe barrel (not shown) is filled by inserting the needle cannula 20 into a container of medicinal fluid to be injected, and the plunger (not shown) of the syringe is drawn in a proximal direction to create an atmospheric pressure within the hub 14 on the proximal side of the valve 42 and filtered element 10. As shown by the flow arrows in FIG. 6, the central opening 48 in the duckbill-configured central portion 46 of valve 42 will open and the medicinal fluid will flow in a proximal direction to fill the hub 14 and the syringe barrel (not shown) when the plunger of the syringe (not shown) is moved in a distal direction to force the medicinal fluid through the filter element 10, the duckbill opening 48 will close to insure that all of the fluid being forced in a proximal direction will pass through the filter element 10 and be filtered en route to the needle cannula 20, as shown by the flow arrows in FIG. 7.

It will thus be appreciated that the combination filter and valve assembly of the present invention provides an efficient, effective and relatively inexpensive means for filtering contaminant from a medicine during the injection step, utilizing a single needle pointed at only one end, without requiring any manual manipulation thereof.

It will be appreciated, of course, that numerous modifications may be made to the exemplary embodiments shown in the drawings and described above without departing from the spirit and scope of the present invention. For example, while the combination filter and valve element of the present invention have been shown in the drawings and described above as incorporated in a needle hub adapted to be retained on the distal end of a hypodermic syringe, it is contemplated that the assembly may be incorporated directly into the syringe barrel. Accordingly, it is intended that the present invention be limited only by the scope of the appended claims.

I claim:

1. In an apparatus for injecting filtered medicinal fluids; said apparatus including a generally tubular member having a chamber therein and a filter element disposed within said chamber; said filter element having a proximal end, a distal end and a central unobstructed passage extending longitudinally therethrough; and valve means operatively associated with said filter element; the improvement comprising:

said valve means being responsive to increased pressure on the distal end of said filter element to open and permit the flow of medicinal fluid through said central unobstructed passage of said filter element; said valve means being responsive to increased pressure on the proximal side of said filter element to block said central passage of said filter element, thereby requiring medicinal fluid under pressure at the proximal end of said filter element to flow through said filter element and be filtered thereby.

2. The combination according to claim 1, wherein said valve means comprises an elastomeric valve member having a central portion extending into said central passage in said filter element, and a slit in said central portion; said slit being opened when said pressure is lower on said proximal side of said filter element; said slit being closed when the pressure is not lower on said proximal side of said filter element.

3. The combination according to claim 2, wherein said central portion of said valve member is of generally hemispherical shape.

4. The combination according to claim 2, wherein said central portion of said valve member is of generally duckbill shape.

5. In a needle cannula-retaining hub having a distal end in which the proximal end of a needle cannula is retained and a proximal end adapted to be retained on the distal end of a hypodermic syringe, and a filter element disposed in said hub between said distal end proximal ends thereof, said filter element having a central unobstructed passage extending therethrough, the improvement comprising:

a valve member normally closing said passage in said filter element; said valve member being responsive to a decreased pressure in the hub on the proximal side of said valve element, relative to the pressure on the distal side of said valve element, to open and permit the flow of medicinal fluid through said central unobstructed passage in said filter element; whereby, when said hub is retained on the distal end of a hypodermic syringe, and when the plunger of such a hypodermic syringe is drawn in a proximal direction in its syringe barrel, when the needle cannula mounted in the distal end of said hub is disposed in a medicinal fluid, said fluid will be drawn through said valve opening and into the syringe barrel, bypassing said filter element; and when the syringe plunger is depressed, said valve member will be closed and the medicinal fluid will be forced through said filter element.

6. The combination according to claim 5, wherein said valve means comprises an elastomeric member having a generally annular skirt portion and a central portion; means defining a slit in said central portion; said central portion extending into said central passage in said filter element.

7. The combination filter and valve according to claim 6, wherein said filter element comprises a generally cylindrical member having a distal end and a proximal end; and wherein said distal end of said filter element has an exterior peripheral wall in relatively tight engagement with the interior wall of said hub; and wherein said filter element further comprises a generally annular distal end surface; and wherein said generally annular skirt portion of said valve overlies said generally annular distal end surface of said filter element in the absence of fluid being forced through said filter element toward the distal end thereof; and further comprising means maintaining said valve member spaced from said distal end of said hub; said means including passage means permitting the flow of medicinal fluid through said distal end of said hub and into the needle cannula mounted therein.

8. An improved filter and valve assembly for insuring that medicinal fluid to be injected into a patient is filtered of contaminants prior to injection, comprising:
   a generally tubular, thermoplastic hub member having a distal end a proximal end; said proximal end of said hub member being adapted to be retained on the distal end of a hypodermic syringe barrel;
   a needle cannula having a proximal end retained in said distal end of said hub member; said proximal end of said needle cannula being unpointed;
   said needle cannula having a pointed distal end adapted to be inserted into a patient;
   a generally cylindrical, porous filter element disposed within said hub member; said filter element having a central passage extending longitudinally therethrough;
   said filter element having a distal end whose outer diameter is enlarged relative to the outer diameter of the remainder of said filter element;
   said enlarged-diameter distal end portion of said filter element fitting snugly against the inner peripheral wall of said hub member so as to prevent medicinal fluid from flowing past said filter element without being filtered thereby;
   a valve member disposed on the distal side of said filter element;
   said valve member including a generally annular skirt portion overlying the distal end surface of said filter element;
   said valve member further including a central section protruding into said central passage of said filter element;
   a slit cut in said central portion of said elastomeric valve member;
   said slit opening in response to a higher pressure on said distal side thereof, relative to the pressure on said proximal side thereof, to permit the flow of fluid therethrough;
   said slit being maintained in a closed position to prevent the flow of medicinal fluid therethrough when the pressure on the proximal side thereof exceeds the pressure on the distal side thereof.

9. An improved technique for filtering medication to be administered to a patient via a hypodermic syringe, comprising the steps of:
   mounting a needle cannula-retaining hub on the distal end portion of a hypodermic syringe barrel, said hub containing a combination filter and valve assembly, said valve being adapted to permit the flow of fluid therethrough from the needle cannula to the syringe barrel when the pressure within the syringe barrel is below the pressure within the needle cannula, said filter having an unobstructed passage extending therethrough;
   inserting the needle cannula into a medication to be injected into a patient;
   withdrawing the plunger of the syringe rearwardly, in a proximal direction within the syringe barrel, to create a reduced pressure state within the barrel as to draw the medication through the needle cannula, through the valve, through said unobstructed passage in said filter, and into the syringe barrel in a substantially unfiltered condition; and thereafter
   withdrawing the needle from the medication container and depressing the plunger in a distal direction in the syringe barrel to force the medication through the filter portion of the filter and valve assembly to filter the medication before it is ejected from the needle cannula.

10. In a valve and filtering device for filtering medicament to be injected into a patient; said device including a housing member having a distal end portion, a proximal end portion, and a chamber disposed between said end portions; filter means and valve means disposed in said chamber; said valve means being operative to permit the flow of medicament from the distal end to the proximal end of said housing member substantially without passing through said filter member; said valve means being operative to require medicament flowing from the proximal end to the distal end of said housing member to pass through said filter member to remove contaminants therefrom prior to injecting such medicament into a patient; the improvement comprising:
   said filter member having an unobstructed passage extending therethrough for permitting the flow of medicament from the distal end of the housing member to the proximal end of the housing member substantially without passing through the filter;
   said valve member having a selectively openable closure aligned with said unobstructed passage; said closure being responsive to relatively increased pressure on the distal side thereof to open and permit medicament to flow through said unobstructed passage and through the proximal end of said housing member; said closure being responsive to relatively increased pressure on the proximal side thereof to close and force medicament flowing from the proximal end of the housing member to flow through the filter member and be filtered thereby before flowing into the distal end of the housing member.

* * * * *